United States Patent [19]
Simon et al.

[11] Patent Number: 5,932,234
[45] Date of Patent: *Aug. 3, 1999

[54] RINSABLE SKINCARE COMPOSITION

[75] Inventors: Pascal Simon, Vitry Sur Seine; Dominique Bordeaux, Saint Michel Sur Orge; Isabelle Afriat, Paris, all of France

[73] Assignee: L'Oreal, Paris, France

[*] Notice: This patent is subject to a terminal disclaimer.

[21] Appl. No.: 08/962,444

[22] Filed: Oct. 31, 1997

[30] Foreign Application Priority Data

Nov. 4, 1996 [FR] France ................................ 96 13404
Apr. 16, 1997 [FR] France ................................ 97 04692

[51] Int. Cl.$^6$ .............................. A61K 7/00; A61K 7/06; A01N 43/04; A01N 43/16

[52] U.S. Cl. ......................... 424/401; 424/70.1; 514/23; 514/458; 514/474; 514/941; 514/944; 536/1.11; 536/18.3

[58] Field of Search .................................. 424/401, 70.1; 514/23, 941, 944, 458, 474; 536/1.11, 18.3

[56] References Cited

U.S. PATENT DOCUMENTS

| | | | |
|---|---|---|---|
| 4,268,498 | 5/1981 | Gedeon et al. | 424/59 |
| 4,482,537 | 11/1984 | El-Menshawy et al. | 424/59 |
| 4,687,843 | 8/1987 | Smolin et al. | 536/18.3 |
| 5,607,980 | 3/1997 | McAtee et al. | 514/476 |
| 5,629,015 | 5/1997 | Ribier et al. | 424/450 |

FOREIGN PATENT DOCUMENTS

| | | |
|---|---|---|
| 0 274 812 A2 | 7/1988 | European Pat. Off. . |
| 0 588 379 A2 | 3/1994 | European Pat. Off. . |
| 2 237 615 | 3/1975 | France . |
| 41 39 935 A1 | 6/1993 | Germany . |
| WO 92/07543 | 5/1992 | WIPO . |
| WO 93/08840 | 5/1993 | WIPO . |
| WO 94/17830 | 8/1994 | WIPO . |

OTHER PUBLICATIONS

Abraham Seldner, "Methyl Glucoside Ethers and Esters in Cosmetic Creams and Lotions", Chemical Abstracts, vol. 93, No. 18, p. 345, Nov. 3, 1980.

*Primary Examiner*—Shelley A. Dodson
*Assistant Examiner*—Marina Lamm
*Attorney, Agent, or Firm*—Oblon, Spivak, McClelland, Maier & Neustadt, P.C.

[57] ABSTRACT

Compositions suitable for cosmetic and/or dermatological use which contain a cosmetic and/or dermatological active agent, at least 20% of a fatty phase, a fatty acid ester of a $C_5$–$C_7$ carbohydrate and polyol.

30 Claims, No Drawings

RINSABLE SKINCARE COMPOSITION

BACKGROUND OF THE INVENTION

1. Field of the Invention

The present invention relates to compositions suitable for application to the skin which contain at least 20% by weight of a fatty phase, a fatty acid ester of a $C_5$–$C_7$ carbohydrate and a polyol. When these compositions also contain cosmetic and/or dermatological active agents, they may be applied to skin in order to treat and/or care for the skin.

2. Description of the Background

Cosmetic and/or dermatological active agents are usually applied to the skin using compositions into which they have been incorporated. These compositions are typically in the form of creams, milks or gels which are spread onto the skin while massaging with the fingertips in order to promote penetration of the composition, and, in particular, penetration of the active agents into the skin. These compositions are usually applied after cleansing the skin, and rinsing of the skin is avoided after they have been applied in order to obtain efficient delivery of the cosmetic and/or dermatological active agents.

This mode of application of cosmetic and/or dermatological active agents is not free of drawbacks. The usual cosmetic and/or dermatological vehicles comprise various cosmetic ingredients including, in particular, surfactants and preserving agents, in appreciable amounts, not only in order to stabilize the cosmetic vehicle but also to dissolve the active agent therein and/or to protect the composition against possible microbial contamination. The repeated and prolonged application of such compositions may result in sensitization of the skin and cause intolerance reactions.

In order to dissolve the active agents, media comprising fatty substances and/or glycols are usually used in skin care products, which impart a certain degree of heaviness to these compositions. Now, some users find it unpleasant to wear a skin care product on the face for several hours, e.g., an entire day, since these products are occasionally considered to be greasy or sticky.

Accordingly, there remains a need for a composition which can be used as a vehicle for cosmetic and/or dermatological active agents, this composition being rinsable, stable, gentle to the skin and having the property of potentiating active agents such that, after applying for a short period, followed by rinsing, the same efficacy of non-therapeutic treatment of the skin than with a leave-on product is obtained, this efficacy being higher than that of other known rinse-off compositions.

SUMMARY OF THE INVENTION

The inventors have discovered, surprisingly, compositions which can be used as vehicles for cosmetic and/or dermatological active agents, these compositions being rinsable and having an efficacy which is comparable, after a short period of application, followed by rinsing, to that of a common leave-on cosmetic and/or dermatological vehicle and higher than that of other known rinse-off products. By incorporating one or more cosmetic and/or dermatological active agent into these vehicles, compositions are obtained which can be used to treat and/or care for skin.

Accordingly, the present invention is directed to compositions containing:

(i) at least 20% by weight of a fatty phase, (ii) at least one fatty ester of a $C_5$–$C_7$ carbohydrate, (iii) at least one polyol, and (iv) at least one cosmetic and/or dermatological active agent.

By applying effective amounts of these compositions to skin, the cosmetic and/or dermatological active agent may be used to treat and/or care for the skin.

The present invention is also directed to formulating the composition described above by combining the cosmetic and/or dermatological active agents with a vehicle composition, most preferably in the form of a stable and visually transparent gel, that contains:

(i) at least 20% by weight of a fatty phase, (ii) at least one fatty ester of a $C_5$–$C_7$ carbohydrate, and (iii) at least one polyol.

A more complete appreciation of the invention and many of the attendant advantages thereof will be readily obtained as the same becomes better understood by reference to the following detailed description.

DETAILED DESCRIPTION OF THE INVENTION

The present invention is based, in part, on the discovery that cosmetic and/or dermatological active agents can be added to a vehicle composition containing (i), (ii) and (iii) to provide compositions which can be used to treat and/or care for skin. Throughout this disclosure, the term "vehicle" refers to a composition containing (i), (ii) and (iii) and optionally, other agents. The vehicle compositions do not contain the skin active agents. Preferably, the vehicle compositions are in the form of a visually transparent gel.

The term "visually transparent" means that the characters printed on a sheet of newspaper can be distinguished through a transparent bottle containing the composition when the sheet is placed behind the bottle. Preferably, the bottle has a size typical for skin care compositions, e.g., 0.5, 1, 2, 3, 4, 5, 6 or 8 fluid oz. In a preferred embodiment, such a bottle has a thickness of 6 to 12 cm, inclusive of all thicknesses therebetween (such as 7, 8, 9, 10 and 11 cm).

The viscosity of the compositions according to the invention is, at room temperature (25° C.) and at normal pressure, preferably greater than 2 Pa.s, more preferably greater than 4 Pa.s and even more preferably greater than 5 Pa.s, e.g., 6, 7, 8, 9, 10, 12, 15, 20 or 25 Pa.s., etc. The viscosity is preferably less than 25 Pa.s. This viscosity may be determined at 25° C. and room pressure with a RHEOMAT 180 (METTLER) at 200 rpm.

The composition according to the invention also preferably contains water. In this case, the composition is preferably in the form of an oil-in-water emulsion having the appearance of a gel.

The term "$C_5$–$C_7$ carbohydrates" refers to pentoses, hexoses and heptoses (non-reduced) and their alkyl-holoside derivatives in which the alkyl group contains from 1 to 6 carbon atoms. The term "alkyl-holoside derivative" includes carbohydrate compounds in which the hydroxyl group at the C-1 carbon atom (i.e., the anomeric carbon atom) is etherified with a $C_1$–$C_6$ alkyl group. Advantageously, the carbohydrates are chosen from those having a chain containing 6 carbon atoms, and they are preferably chosen from glucose, fructose and their $C_1$–$C_6$ alkyl-glucoside and alkyl-fructoside derivatives. Even more preferably, the carbohydrate is glucose or an alkyl-glucoside derivative such as 1-methylglucoside, for example.

The term "fatty esters of $C_5$–$C_7$ carbohydrates" refers to compounds obtained by reaction of a fatty acid containing a saturated or unsaturated chain having from 8 to 30 carbon atoms, preferably from 12 to 22 carbon atoms and even more preferably from 16 to 20 carbon atoms, with a carbohydrate chosen from pentoses, hexoses, heptoses and their alkylholoside derivatives in which the alkyl group contains from 1 to 6 carbon atoms. The fatty acid ester of the carbohydrate may contain a mixture of mono-, di-, tri- and tetra-ester derivatives.

Advantageously, the fatty $C_5$–$C_7$ carbohydrate esters are oxyalkylenated. Preferably, the $C_5$–$C_7$ carbohydrate esters are etherified by one or more oxyethylene and/or oxypropylene groups, the oxyethylene or oxypropylene substituents together representing in total from 5 to 200, and preferably 15 to 150, alkylene oxide units. These ranges include all specific values and subranges therebetween, such as 6, 7, 8, 10, 20, 25, 30, 40, 50, 75, 100, 125, 150 and 175 oxyethylene and/or oxypropylene groups.

Preferably, all of the hydroxyl functions of the carbohydrate derivatives used in the compositions according to the invention are substituted with an ester group or with an alkylene oxide group. Such compounds are well known to those skilled in the art. Several of these compounds are commercially available. For example, the derivatives sold under the brand Glucamate by the Amerchol Company can be used.

In a preferred embodiment, the fatty $C_6$ carbohydrate esters are represented by formula (I):

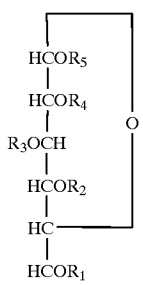
(I)

where
$R_1$ is a group having formula (III):

(III)

$R'$ is a linear or branched, saturated or unsaturated $C_8$–$C_{30}$, and preferably a $C_{12}$–$C_{22}$, alkyl group, $R_2$, $R_3$ and $R_4$, which may be identical or different, are:
a hydrogen atom,
a group having formula (II):

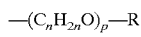
(II)

with n=2 or 3; p is an integer from 2 to 50; R is a hydrogen atom or a $C_1$–$C_6$ alkyl group,
a group having formula (III):

(III)

where $R'$ is linear or branched, saturated or unsaturated $C_8$–$C_{30}$, and preferably a $C_{12}$–$C_{22}$, alkyl group, where
at least one from among $R_2$, $R_3$ and $R_4$ has formula (II), and the total number of the oxyalkylenated residues, $\Sigma p$, is 5 to 200, $R_5$ is a linear or branched, saturated or unsaturated $C_1$–$C_6$ alkyl group.

In a preferred embodiment, the variables defined above have the following meanings:
$R_5$=$CH_3$,
at least two groups from among $R_2$, $R_3$ and $R_4$ have formula (II),
$\Sigma p$ is 15 to 150,
R=H,
$R'$ is a $C_{16}$–$C_{20}$ alkyl group, and
none of the groups $R_2$, $R_3$ or $R_4$ is a hydrogen atom.

Preferably, the compositions according to the invention comprise, by weight % relative to the total weight of the composition, from 0.5 to 50% of the fatty $C_5$–$C_7$ carbohydrate ester, and more preferably from 2 to 20%. These ranges include all specific values and subranges therebetween, including 0.75, 1.0, 1.25, 1.5, 1.75, 3, 4, 5, 10, 15, 25, 30, 35, 40 and 45% by weight of the fatty acid $C_5$–$C_7$ carbohydrate ester.

The compositions according to the invention contain at least one polyol. This polyol may optionally be oxyalkylenated. Advantageously, the polyol comprises at least two free hydroxyl functions. The polyol may be chosen from ethylene glycol, propylene glycol, 1,3-butylene glycol, dipropylene glycol, glycerol, polyglycerols such as diglycerol, triglycerol and tetraglycerol, glucose, maltose, maltitol, sucrose, fructose, sorbitol, sugars derived from the decomposition of starch and their mixtures.

The polyol preferably represents from 0.5 to 60% by weight, relative to the total weight of the composition, more preferably from 2 to 40% and most preferably from 5 to 30%. These ranges include all specific values and subranges therebetween, including 0.75, 1.0, 1.25, 1.5, 1.75, 2.5, 3, 4, 6, 10, 15, 20, 25, 35, 45, 50 and 55% by weight polyol.

The nature of the fatty phase forming part of the composition of the emulsions according to the invention is not particularly limited. The fatty phase may contain any of the well-recognized compounds which are suitable for the manufacture of emulsions of oil-in-water type for application to the skin. In particular, these compounds may be used, alone or as mixtures, from the various fatty substances, oils of plant, animal or mineral origin, natural or synthetic waxes, and the like.

Among the oils which may be used in the present invention, mention may be made of oils of plant or animal origin such as, for example, squalane, coconut oil, macadamia oil, mink oil, turtle oil, soybean oil, grapeseed oil, sesame oil, corn oil, rapeseed oil, sunflower oil, cottonseed oil, avocado oil, olive oil, castor oil, jojoba oil, groundnut oil; hydrocarbon oils such as liquid paraffins, isoparaffins, petroleum jelly; silicone oils such as polydimethylsiloxanes, cyclopolydimethylsiloxanes, polymethylphenylsiloxanes, polysiloxanes modified with fatty acids, polysiloxanes modified with fatty alcohols, polysiloxanes modified with polyoxyalkylenes, fluorosilicones; perfluoro and/or organofluoro oils; higher fatty acids such as myristic acid, palmitic acid, stearic acid, behenic acid, oleic acid, linoleic acid, linolenic acid, isostearic acid, higher fatty alcohols such as cetanol, stearyl alcohol, oleyl alcohol; mono- and diesters, among which mention may be made in particular of isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, 2-diethylhexyl succinate, diisostearyl malate, 2-octyldodecyl lactate, glyceryl triisostearate, di-n-butyl adipate, bis(2-ethylhexyl) adipate, ethylene glycol dioleate, ethylene glycol diisotridecanoate, ethylene glycol diisostearate, neopentyl glycol dicaprylate. An oil or a mixture of oils having a refractive index $^{20}n_D$ 1.45 is preferably used.

The fatty phase may represent from 20 to 95% by weight of the total weight of the composition, preferably from 20 to 85% and even more preferably from 40 to 80%. These ranges include all specific values and subranges therebetween, including 25, 30, 35, 45, 50, 55, 60, 65, 70, 75 and 90% by weight of the fatty phase.

Water preferably represents from 0.01 to 30% by weight relative to the total weight of the composition. More preferably, water represents from 2 to 20% by weight relative to the total weight of the composition. These ranges include all specific values and subranges therebetween, including 0.05, 0.1, 0.25, 0.5, 0.75, 1, 1.5, 3, 5, 10, 15 and 25% by weight of water.

Usually, water is understood to mean pure water. However, at least some of the water used in the compositions according to the invention may be mineral waters or spring waters. In general, a mineral water is fit for consumption, which is not always the case for a spring water. Each of these waters contains, inter alia, dissolved minerals and trace elements. These waters are known to be used for purposes of specific treatment depending on the specific trace elements and minerals that they contain, such as the moisturization and desensitization of the skin or the treatment of certain dermatitides. The expression mineral waters or spring waters will be understood to denote not only natural mineral waters or spring waters but also natural mineral waters or spring waters enriched with additional mineral and/or trace-element constituents, as well as aqueous solutions of minerals and/or trace elements prepared from purified water (demineralized or distilled water).

A natural spring water or mineral water used according to the invention may, for example, be chosen from eau de Vittel, waters from the Vichy bassin, eau d'Uriage, eau de la Roche Posay, eau de la Bourboule, eau d'Enghien-les-Bains, eau de Saint Gervais-les-Bains, eau de Néris-les-Bains, eau d'Allevard-les-Bains, eau de Digne, eau de Maizières, eau de Neyrac-les-Bains, eau de Lons-le-Saunier, les Eaux Bonnes, eau de Rochefort, eau de Saint Christau, eau des Fumades, eau de Tercis-les-bains, eau d'Uriage-les-bains and eau d'Avenne.

The cosmetic compositions of the invention may also contain water-soluble or liposoluble adjuvants that are commonly used in the cosmetic field, such as preserving agents, antioxidants, fragrances, sunscreens, dyestuffs and pearlescent agents.

The compositions according to the invention also contain at least one cosmetic and/or dermatological active agent chosen, for example, from antiwrinkle, anti-ageing, moisturizing, depigmenting, keratolytic, slimming, tonifying, anti-acne, antiseborrhic, anti-inflammatory, self-tanning, anti-free-radical and firming active agents and active agents for treating skin diseases such as mycosis, dermatitis and psoriasis. Depending on its hydrophilic or lipophilic nature, this active agent is present in the aqueous phase or in the fatty phase, or both phases. Preferably, these active agents are introduced into the vehicle in a proportion of from 0.001 to 15% by weight relative to the total weight of the composition, more preferably 0.1 to 10% by weight. These ranges includes all specific values and subranges therebetween, including 0.002, 0.005, 0.008, 0.01, 0.05, 0.15, 0.2, 0.3, 0.5, 1, 2, 3, 4, 5, 6, 7, 8, 9, 11, 12, 13 and 14% by weight of the active agent or combination thereof.

Among the active agents which may be used in the present invention, mention may be made, for example, of: ascorbic acid and esters thereof, allantoin, citric acid, caffeic acid, salicylic acid and its derivatives (for example 5-n-octanoylsalicylic acid or 5-decanoylsalicylic acid), α-hydroxy acids such as lactic acid, methyllactic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetra-ecosanoic acid, 2-hydroxyeicosanoic acid and mandelic acid, benzoic acid, phenyllactic acid, gluconic acid, galacturonic acid, aleuritic acid, ribonic acid, tartronic acid, tartaric acid, malic acid, fumaric acid, retinoic acid and its derivatives, benzene-1,4-bis(3-methylidene-10-camphorsulphonic acid), dihydroxyacetone (DHA), water-soluble vitamins, starch, bacterial or plant extracts, in particular Aloe vera, tocopherol (vitamin E) and its derivatives, essential fatty acids, ceramides, essential oils. Any natural or synthetic compound containing such acids may also be used, such as plant extracts and more especially fruit extracts. Plant proteins and their hydrolysates may also be used. It is also possible to dissolve xanthic derivatives (caffeine, theophylline), β-glycyrrhetinic acid, asiatic acid, octopirox or alternatively retinol and its esters, and natural derivatives of the flavonoid family. Agents which modify skin differentiation and/or proliferation and/or pigmentation may also be used in the present invention, such as vitamin D and its derivatives, oestrogens such as oestradiol, kojic acid or hydroquinone; anti-free-radical agents such as α-tocopherol or its esters, superoxide dismutases, certain metal-chelating agents; antagonists of substance P and/or of CGRP (calcitonin gene related peptide) such as Iris pallida and strontium salts, in particular strontium chlorides and nitrates, or antagonists of substance P and/or of CGRP such as those described in French patent applications FR-A-2,719,474 and FR-A-2,729,855, herein.

Preferably, the active agents are chosen from ascorbic acid and esters thereof, kojic acid, citric acid, caffeic acid, salicylic acid, lactic acid, glycolic acid, malic acid, dihydroxyacetone and α-tocopherol and esters thereof.

The active agents may also be chosen from enzymes, in particular from proteases.

It is known to introduce enzymes into cosmetic and/or dermatological compositions, and in particular proteases used for their proteolytic properties. These enzymes are desired in the cosmetic field for their smoothing and cleansing power, and their ability to remove dead cells from the skin.

Unfortunately, enzymes have the drawback of being unstable in aqueous media and of being readily degraded or modified under the influence of water. They thus rapidly lose their activity over time and this instability is contrary to the desired efficacy.

In the compositions according to the invention, when the active agent is an enzyme, it has been observed that it was stabilized and retained its activity over time. Preferably, the proportion of the various components are selected such that the value for the activity in water of the composition is at most 0.7.

The activity in water, $a_w$, of a medium containing water is the ratio of the vapor pressure of water for the product "$P_{H2O\ product}$" and the vapor pressure of pure water "$P_{H2O\ pure}$" at the same temperature. It may also be expressed as the ratio of the number of moles of water "$N_{H2O}$" to the total number of moles "$N_{H2O} + N_{dissolved\ substances}$", which takes into account the number of moles of dissolved substances "$N_{dissolved\ substances}$".

It is calculated according to the following formulae:

$$a_w = \frac{P_{H2O\ product}}{P_{H2O\ pure}} = \frac{N_{H2O}}{N_{H2O} + N_{dissolved\ substances}}$$

Various methods may be used to measure the water activity. The most common is the manometric method by which the vapour pressure is measured directly.

Conventional cosmetic or dermatological compositions have a water activity of about 0.95 to 0.99. A water activity below 0.85 represents an appreciable decrease in water activity. Only compositions having a water activity value which is at most 0.85 provide good conservation of the enzymatic activity of the enzymes.

The enzymes used according to the invention are, in particular, lactoperoxidases, lipases, proteases, phospholipases and cellulases.

The enzyme(s) used according to the invention is/are advantageously a protease. They may be chosen, for example, from those sold under the trade name "Subtilisin SP 544" by the company Novo Nordisk and that sold under the trade name "Lysoveg" by the company Laboratoires Sérobiologiques de Nancy.

In the composition according to the invention, the enzyme may advantageously be used in an amount ranging from 0.001 to 15% by weight, preferably from 0.01 to 10% by weight and better still from 0.05 to 5% by weight, relative to the total weight of the composition. These ranges include all specific values and subranges therebetween, including 0.002, 0.005, 0.01, 0.02, 0.08, 0.1, 0.2, 0.5, 1, 2, 3, 4, 6, 7, 8, 9, 11, 12, 13 and 14% by weight of the enzymes.

The compositions according to the invention may also contain insoluble fillers: polyethylene powder, polyamide particles such as, for example, those sold under the name "Orgasol" by the company Atochem, also known under the names (CTFA) "polyamide 12" or "polyamide 6". Kaolin, nylon powders referred to under the CTFA name of "nylon 12" or "nylon 6" may also be used in these compositions. Such compositions are advantageous in cleansing the skin on account of their exfoliant properties.

The compositions according to the invention preferably have the property of potentiating the active agents they contain such that these active agents have the same efficacy in the compositions according to the invention after a very short period of application and then rinsing, as compared to a composition which is applied for several hours. The inventive compositions have the advantage of being more comfortable than such leave-on care compositions. The mode of application makes it possible to obtain, for example, a non-therapeutic skin treatment which is more uniform when compared with leave-in compositions. This result is particularly advantageous in the case of self-tanning treatments, since leave-in compositions often have the disadvantage of producing irregular tanning on account of a non-uniform application, which is difficult to control.

The vehicles according to the invention preferably have the appearance of a stable transparent gel. Depending on the properties of the active agents, in particular their ease of dissolution in the vehicle, a transparent skin care composition may be obtained, but a non-transparent care composition may also be obtained, on account of the insolubility of the active agents in the vehicle or because compounds have been incorporated therein which remove its transparency, such as, for example, pearlescent agents or fillers. In addition, these compositions can be rinsed out very well. In particular, the fatty esters of $C_5$ to $C_7$ carbohydrates give these compositions improved rinsability as compared to compositions based on sucrose esters and those based on sorbitol esters.

In a preferred embodiment, the compositions according to the invention are in the form of a cleansing and/or make-up-removing product, a mask, a scrubbing product or an exfoliant.

To treat and/or care for skin with the compositions of the present invention, an effective amount of the composition is applied to the skin and then left in contact with the skin for the desired time period. If desired, the composition may be rinsed from the skin with water. The effective amount of the composition may, and the length of time for contacting the skin, may depend on the nature of the active agent contained therein. These parameters may be determined by simple experiments.

Having generally described this invention, a further understanding can be obtained by reference to certain specific examples which are provided herein for purposes of illustration only and are not intended to be limiting unless otherwise specified.

EXAMPLES

A cosmetic test was carried out to illustrate the advantage, in terms of efficacy and comfort, of the vehicles according to the invention with, as active agent, a mixture of a-hydroxy acids (lactic acid, glycolic acid, citric acid, malic acid and tartaric acid). A panel of 11 individuals compared a composition according to the invention with a standard cleansing/make-up-removing milk. The two formulae contained the same level of active agents, introduced, according to an identical procedure, into the aqueous phase of the compositions.

For each composition, the percentages are given by weight of active material relative to the total weight of the composition.

Composition 1 (According to the Invention)

| A) Aqueous phase | |
|---|---|
| Oxyethylenated (20 EO) methylglucose sesquistearate marketed under the brand name Glucamate SSE 20 | 4.5% |
| Glycerol | 10% |
| Mixture of fruit acids (glycolic acid, lactic acid, malic acid, tartaric acid) | 1% |
| Water | 8% |
| Preserving agents | qs |
| B) Oily phase | |
| Cyclomethicone | 18% |
| Isopropyl myristate | 12% |
| Isoparaffin | 30% |
| Isobutylene | 16% |
| C) Fragrance | 0.5% |

Procedure: the glucose derivative was dissolved in the water and the polyols with stirring between 25° C. and 35° C. until a homogeneous viscous paste was obtained. The oily phase and the fragrance are then introduced slowly with vigorous stirring. The product was then smoothed out with a paddle and degassed under vacuum.

Composition 2 (Comparative Example)

| A) Aqueous phase | |
| --- | --- |
| Oxyethylenated (20 EO) methylglucose sesquistearate marketed under the brand name Glucamate SSE 20 | 2% |
| Methylglucose sesquistearate marketed under the brand name Glucate SS | 2% |
| Glycerol | 4% |
| Mixture of fruit acids (glycolic acid, lactic acid, malic acid, tartaric acid) | 1% |
| Carbomer | 0.3% |
| Preserving agents | 0.4% |
| Water | qsp 100 |
| B) Oily phase | |
| Stearyl alcohol | 1.3% |
| Cyclomethicone | 8% |
| Sesame oil | 5% |
| Isobutylene | 3% |
| C) Fragrance | 0.2% |

A make-up-removing milk was prepared in the form of an oil-in-water emulsion from all of the above components.

The composition of Example 1, containing 76% fatty phase, and that of Comparative Example 2, containing 17.3% fatty phase, were tested on a panel of 11 individuals in the following way:

The 11 individuals applied the 2 products to half of the face each, in order to thoroughly compare the effects; each person left the product on their face for an exposure time of 10 minutes before rinsing it off and drying the face.

The users were questioned as regards the discomfort experienced during and after the application, and regarding the effects of the two compositions after application. The result was as follows:

Discomfort: number of users complaining of redness, stinging, heating, dryness of the skin, itching and burning:
  before rinsing
    7/11 individuals for the standard milk formula (composition 2),
    3/11 individuals with the composition of the invention (composition 1).
  after rinsing:
    10/11 individuals for the standard milk formula (composition 2),
    2/11 individuals with the composition according to the invention (composition 1).

Efficacy:
More uniform skin:
Response:
  yes:
    2/11 individuals for the standard milk formula (composition 2),
    7/11 individuals with the composition of the invention (composition 1),
  no:
    6/11 individuals for the standard milk formula (composition 2),
    2/11 individuals with the composition of the invention (composition 1).

Clearer skin:
Response:
  yes:
    3/11 individuals for the standard milk formula (composition 2),
    4/11 individuals with the composition of the invention (composition 1),
  no:
    5/11 individuals for the standard milk formula (composition 2),
    3/11 individuals with the composition of the invention (composition 1).

Softer skin:
Response:
  yes:
    2/11 individuals for the standard milk formula (composition 2),
    8/11 individuals with the composition of the invention (composition 1), These comparative tests underline the superiority of the compositions according to the invention over the rinsable comparative compositions, both in terms of harmlessness and efficacy.

EXAMPLES OF THE COMPOSITIONS

For each composition, the percentages are given by weight of active material relative to the total weight of the composition.

The viscosity is measured at 25° C. using a Rheomat 180 viscometer; the viscosity measurements are given in Pascal seconds (Pa.s).

Example 1

| A) Aqueous phase | |
| --- | --- |
| Oxyethylenated (120 EO) methylglucose dioleate | 3% |
| Oxyethylenated (20 EO) methylglucose sesquistearate | 1% |
| Glycerol | 15% |
| Glycolic acid | 2% |
| Water | 4% |
| B) Oily phase | |
| Liquid petroleum jelly | 10% |
| 2-Ethylhexyl palmitate | 23.5% |
| Hydrogenated isoparaffin | 9% |
| Cyclopentadimethylsiloxane | 14% |
| Tetramethyl hexane-heptane-octane | 18.5% |
| Fragrance | qs |

Procedure: the glucose derivative was dissolved in the water and the polyols with stirring between 25° C. and 35° C. until a homogeneous viscous paste was obtained. The oily phase and the fragrance were then introduced slowly with vigorous stirring. The product was then smoothed out with a paddle and degassed under vacuum.

This composition had a crystalline, transparent, gelled appearance which was visually very appealing. It had a Rheomat viscosity of 9 Pa.s.

The products are easy to spread on the skin and their rinsability is excellent. After rinsing, the skin is clean and has a silky, non-greasy feel.

Example 2

| A) Aqueous phase: | |
| --- | --- |
| Oxyethylenated (120 EO) methylglucose dioleate | 6% |
| Oxyethylenated (20 EO) methylglucose sesquistearate | 2% |
| Glycerol | 11% |
| PEG-20 | 6% |
| Dihydroxyacetone | 10% |
| Water | 5% |

-continued

| B) Fatty phase: | |
|---|---|
| Liquid petroleum jelly | 12% |
| Hydrogenated isoparaffin | 26% |
| Cyclomethicone | 22% |

This composition had a crystalline, transparent, gelled appearance which is visually very appealing. It had a Rheomat viscosity of 9 Pa.s.

After an exposure time of 10 min followed by rinsing, a mark-free uniform tan was observed. Daily repetition of this cosmetic treatment allowed this tan to develop smoothly, giving it the appearance of a natural tan.

Example 3

| A) Aqueous phase: | |
|---|---|
| Oxyethylenated (20 EO) methylglucose sesquistearate marketed under the brand name Glucamate SSE 20 | 4.5% |
| Glycerol | 10% |
| Subtilisin SP544 | 0.1% |
| Water | 8.5% |
| Preserving agents | qs |
| B) Oily phase | |
| Cyclomethicone | 18% |
| Isopropyl myristate | 12% |
| Isoparaffin | 30% |
| Isobutylene | 16% |
| C) Fragrance | 0.5% |

This composition had a crystalline, transparent, gelled appearance which was visually very appealing. This composition was able to facilitate the removal of cells from the skin and to lighten the complexion.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A cosmetic or dermatological composition consisting essentially of:
   (i) at least 20% by weight of a fatty phase,
   (ii) at least one fatty ester of a $C_5$–$C_7$ carbohydrate,
   (iii) at least one polyol, and
   (iv) at least one cosmetic and/or dermatological active agent.

2. The composition of claim 1, which is a gel.

3. The composition of claim 1, wherein the $C_5$–$C_7$ carbohydrate is a member selected from the group consisting of a pentose, a hexose and a heptose, or is a member selected from the group consisting of an alkyl holoside derivative of a pentose, a hexose and pentose wherein the alkyl group has 1 to 6 carbon atoms.

4. The composition of claim 1, wherein the carbohydrate is 1-methylglucoside.

5. The composition of claim 1, wherein the fatty ester of a $C_5$–$C_7$ carbohydrate is a compound obtained by reaction of a fatty acid containing a saturated or unsaturated chain having from 8 to 30 carbon atoms, with the carbohydrate.

6. The composition of claim 1, wherein the fatty ester of $C_5$–$C_7$ carbohydrate is oxyalkylenated.

7. The composition of claim 1, wherein the fatty ester of a $C_5$–$C_7$ carbohydrate is etherified by one or more oxyethylene and/or oxypropylene groups, wherein the total number of the oxyethylene and/or oxypropylene groups is 5 to 200.

8. The composition of claim 1, wherein the fatty ester of a carbohydrate is a compound having formula (I):

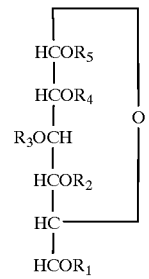

wherein
$R_1$ has formula (III):

wherein
R' is a linear or branched, saturated or unsaturated $C_8$–$C_{30}$ alkyl group,
$R_2$, $R_3$ and $R_4$, which may be the same or different, each represent:
a hydrogen atom,
a group having formula (II):

wherein n is 2 or 3; p is an integer from 2 to 50; R is a hydrogen atom or a $C_1$–$C_6$ alkyl group, or
a group having formula (III):

wherein R' is linear or branched, saturated or unsaturated $C_8$–$C_{30}$ alkyl group,
wherein
at least one from among $R_2$, $R_3$ and $R_4$ is the group having formula (II), and the total of the oxyalkylenated residues, $\Sigma p$, is 5 to 200, and
$R_5$ is a linear or branched, saturated or unsaturated $C_1$–$C_6$ alkyl group.

9. The composition of claim 9, wherein
$R_5$ is $CH_3$,
at least two groups from among $R_2$, $R_3$ and $R_4$ have formula (II),
$\Sigma p$ is 15 to 150;
R is H,
at least one group from among $R_1$, $R_2$, $R_3$ and $R_4$ has formula (III);
R' is a $C_{16}$–$C_{20}$ alkyl group; and
none of the groups $R_2$, $R_3$ or $R_4$ is a hydrogen atom.

10. The composition of claim 1, comprising 0.5 to 50% by weight, relative to the total weight of the composition, of the fatty ester of a $C_5$–$C_7$ carbohydrate.

11. The composition of claim 1, wherein the polyol comprises at least one member selected from the group consisting of ethylene glycol, propylene glycol, 1,3-butylene glycol, dipropylene glycol, glycerol, diglycerol, triglycerol and tetraglycerol, glucose, maltose, maltitol, sucrose, fructose, sorbitol, and sugars derived from the decomposition of starch and mixtures thereof.

12. The composition of claim 1, comprising 0.5 to 60% by weight, relative to the total weight of the composition, of the polyol.

13. The composition of claim 1, wherein the fatty phase comprises an oil or a mixture of oils having a refractive index $^{20}n_D \leq 1.45$.

14. The composition of claim 1, comprising 20 to 95% by weight, relative to the total weight of the composition, of the fatty phase.

15. The composition of claim 1, wherein the cosmetic and/or dermatological active agent is a member selected from the group consisting of a depigmenting, keratolytic, slimming, tonifying, anti-acne, antiseborrheic, anti-inflammatory, self-tanning, anti-free-radical, a firming active agent, or an active agent for treating a skin disease.

16. The composition of claim 1, comprising 0.1 to 10% by weight, based on the total weight of the composition, of the cosmetic and/or dermatological active agent.

17. The composition of claim 1, wherein the cosmetic and/or dermatological active agent is selected from the group consisting of ascorbic acid and esters thereof, kojic acid, citric acid, caffeic acid, salicylic acid, lactic acid, glycolic acid, malic acid, dihydroxyacetone and α-tocopherol and esters thereof.

18. The composition of claim 1, wherein the cosmetic and/or dermatological active agent is an enzyme.

19. The composition of claim 18, wherein the enzyme is a member selected from the group consisting of a lactoperoxidase, a lipase, a protease, a phospholipase and a cellulase.

20. The composition of claim 19, wherein the enzyme is a protease.

21. The composition of claim 18, comprising 0.001 to 15% by weight, based on the total weight of the composition, of the enzyme.

22. The composition of claim 18, wherein the water activity of the composition is at most 0.85.

23. The composition of claim 22, wherein the water activity of the composition is at most 0.7.

24. The composition of claim 1, which is a cleansing and/or make-up-removing product, a mask, a scrubbing product or an exfoliant.

25. A method of making the composition of claim 1, comprising combining (i), (ii), (iii) and (iv) to produce the composition.

26. A method of treating skin, comprising applying to the skin an effective amount of the composition of claim 1.

27. A cosmetic or dermatological composition, consisting essentially of:
 (i) at least 20% by weight of a fatty phase,
 (ii) at least one fatty ester of a $C_5$–$C_7$ carbohydrate,
 (iii) at least one polyol,
 (iv) at least one cosmetic and/or dermatological active agent, and
 (v) water.

28. The composition of claim 27, wherein the amount of water ranges from 0.01 to 30 wt. %.

29. The composition of claim 27, wherein the water is mineral or spring water.

30. A cosmetic or dermatological composition, consisting essentially of:
 (i) at least 20% by weight of a fatty phase,
 (ii) at least one fatty ester of a $C_5$–$C_7$ carbohydrate,
 (iii) at least one polyol,
 (iv) at least one cosmetic and/or dermatological active agent,
 (v) water, and
 (vi) at least one cosmetic or dermatologically acceptable adjuvant.

* * * * *